(12) United States Patent
Pratt et al.

(10) Patent No.: US 11,154,651 B2
(45) Date of Patent: *Oct. 26, 2021

(54) REDUCED-PRESSURE TREATMENT SYSTEMS WITH RESERVOIR CONTROL

(71) Applicant: KCI Licensing, Inc., San Antonio, TX (US)

(72) Inventors: Benjamin Andrew Pratt, Poole (GB); Christopher Brian Locke, Bournemouth (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 496 days.

This patent is subject to a terminal disclaimer.

(21) Appl. No.: 16/157,755

(22) Filed: Oct. 11, 2018

(65) Prior Publication Data

US 2019/0060536 A1  Feb. 28, 2019

Related U.S. Application Data

(60) Continuation of application No. 14/148,320, filed on Jan. 6, 2014, now Pat. No. 10,124,097, which is a
(Continued)

(51) Int. Cl.
*A61M 1/00* (2006.01)

(52) U.S. Cl.
CPC .............. *A61M 1/90* (2021.05); *A61M 1/74* (2021.05); *A61M 1/78* (2021.05); *A61M 1/784* (2021.05);
(Continued)

(58) Field of Classification Search
CPC combination set(s) only.
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Extended European Search Report for corresponding Application No. 172019945, dated Mar. 22, 2018.
(Continued)

*Primary Examiner* — Guy K Townsend

(57) ABSTRACT

A reduced-pressure system for delivering reduced pressure for medical purposes to a desired site and to receive fluids in one instance includes a reservoir having an interior space operable to contain the fluids. A reduced-pressure delivery conduit is placed in fluid communication with the interior space for delivering the reduced pressure to the desired site. A source conduit and a pressure sensor conduit are placed in fluid communication with the interior space. A pressure sensor is placed in fluid communication with the pressure sensor conduit. A reduced-pressure source is placed in fluid communication with the source conduit. A reduced-pressure control unit is associated with the pressure sensor and the reduced-pressure source and is operable to receive pressure data from the pressure sensor and supply data from the reduced-pressure source and to determine when a reservoir-full/blockage condition exists. Other systems and methods are presented.

14 Claims, 5 Drawing Sheets

Related U.S. Application Data division of application No. 13/724,876, filed on Dec. 21, 2012, now Pat. No. 8,652,111, which is a division of application No. 12/537,797, filed on Aug. 7, 2009, now Pat. No. 8,366,691.

(60) Provisional application No. 61/087,377, filed on Aug. 8, 2008.

(52) U.S. Cl.
CPC .... *A61M 2205/3382* (2013.01); *Y10T 29/494* (2015.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A * | 12/1987 | McNeil | A61M 1/74 604/67 |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,562,615 A * | 10/1996 | Nassif | A61M 5/16831 604/67 |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 6,824,533 B2 | 11/2004 | Risk, Jr. et al. | |
| 7,846,141 B2 | 12/2010 | Weston | |
| 7,927,319 B2 * | 4/2011 | Lawhorn | A61M 1/90 604/313 |
| 8,062,273 B2 | 11/2011 | Weston | |
| 8,216,198 B2 | 7/2012 | Heagle et al. | |
| 8,235,972 B2 * | 8/2012 | Adahan | F04B 43/067 604/540 |
| 8,251,979 B2 | 8/2012 | Malhi | |
| 8,257,327 B2 | 9/2012 | Blott et al. | |
| 8,366,691 B2 * | 2/2013 | Pratt | A61M 1/90 604/318 |
| 8,398,614 B2 | 3/2013 | Blott et al. | |
| 8,409,170 B2 * | 4/2013 | Locke | A61M 1/90 604/540 |
| 8,444,612 B2 * | 5/2013 | Patel | A61M 1/80 604/313 |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,652,111 B2 * | 2/2014 | Pratt | A61M 1/78 604/318 |
| 8,679,081 B2 | 3/2014 | Heagle et al. | |
| 8,834,451 B2 | 9/2014 | Blott et al. | |
| 8,905,985 B2 * | 12/2014 | Allen | A61M 1/74 604/319 |
| 8,926,592 B2 | 1/2015 | Blott et al. | |
| 8,951,235 B2 * | 2/2015 | Allen | A61M 1/743 604/319 |
| 9,017,302 B2 | 4/2015 | Vitaris et al. | |
| 9,084,845 B2 * | 7/2015 | Adie | A61M 1/90 604/540 |
| 9,138,515 B2 * | 9/2015 | Locke | A61M 1/90 604/540 |
| 9,198,801 B2 | 12/2015 | Weston | |

(56) References Cited

U.S. PATENT DOCUMENTS

| | | | |
|---|---|---|---|
| 9,211,365 B2 | 12/2015 | Weston | |
| 9,289,542 B2 | 3/2016 | Blott et al. | |
| 10,124,097 B2* | 11/2018 | Pratt | A61M 1/90 604/540 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2003/0040687 A1* | 2/2003 | Boynton | A61M 1/74 601/6 |
| 2003/0093041 A1* | 5/2003 | Risk, Jr. | A61M 27/00 604/308 |
| 2006/0025727 A1 | 2/2006 | Boehringer et al. | |
| 2007/0032762 A1* | 2/2007 | Vogel | A61M 1/782 604/305 |
| 2007/0032763 A1 | 2/2007 | Vogel | |
| 2008/0200857 A1* | 8/2008 | Lawhorn | G08B 31/00 602/41 |
| 2008/0234641 A1* | 9/2008 | Locke | A61M 1/74 604/313 |
| 2009/0030402 A1* | 1/2009 | Adahan | A61M 1/964 604/540 |
| 2009/0187131 A1* | 7/2009 | Fitzgerald | A61M 1/84 604/6.09 |
| 2010/0150991 A1* | 6/2010 | Bernstein | A61K 31/00 424/447 |
| 2011/0130712 A1* | 6/2011 | Topaz | A61M 1/74 604/23 |
| 2012/0136325 A1* | 5/2012 | Allen | A61M 1/75 604/319 |
| 2012/0165764 A1* | 6/2012 | Allen | A61M 1/743 604/319 |
| 2012/0271256 A1* | 10/2012 | Locke | A61M 1/742 604/319 |
| 2013/0110058 A1* | 5/2013 | Adie | A61M 1/78 604/319 |
| 2013/0172805 A1* | 7/2013 | Truckai | A61M 3/0216 604/28 |
| 2013/0172839 A1* | 7/2013 | Locke | A61M 1/732 604/319 |
| 2013/0331823 A1* | 12/2013 | Askem | A61M 1/90 604/543 |
| 2014/0115893 A1* | 5/2014 | Pratt | A61M 1/784 29/890.09 |
| 2014/0163491 A1 | 6/2014 | Schuessler et al. | |
| 2015/0051560 A1* | 2/2015 | Askem | A61M 1/75 604/319 |
| 2015/0065966 A1* | 3/2015 | Adie | A61M 1/78 604/318 |
| 2015/0080788 A1 | 3/2015 | Blott et al. | |
| 2015/0100045 A1* | 4/2015 | Allen | A61M 1/82 604/543 |
| 2015/0174304 A1* | 6/2015 | Askem | A61M 1/732 604/319 |
| 2015/0217032 A1* | 8/2015 | Allen | A61M 39/22 604/319 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| JP | 04362712 B2 | 11/2009 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 0061206 A1 | 10/2000 |
| WO | 2003101508 A2 | 12/2003 |
| WO | 2007019038 A2 | 2/2007 |
| WO | 2007088530 A1 | 8/2007 |
| WO | 2008036360 A2 | 3/2008 |
| WO | 2008039314 A2 | 4/2008 |
| WO | 2008049029 A2 | 4/2008 |

OTHER PUBLICATIONS

Canadian Examiner's Report for corresponding Application No. 2937100, dated May 3, 2018.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philiadelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/the British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.

(56) References Cited

OTHER PUBLICATIONS

Davydov, Yu.A., et al; "Bacteriological and Cytological Assessment of Vacuum Therapy for Purulent Wounds"; Vestnik Khirugi, Oct 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", the Lancet, Sep. 3, 1983, pp. 532-534.
Chinn, Steven D. et al.: "Closed Wound Suction Drainage", the Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

REDUCED-PRESSURE TREATMENT SYSTEMS WITH RESERVOIR CONTROL

CROSS REFERENCE TO RELATED APPLICATIONS

This application is a continuation of U.S. patent application Ser. No. 14/148,320, filed Jan. 6, 2014, which is a divisional of U.S. patent application Ser. No. 13/724,876, filed Dec. 21, 2012, now U.S. Pat. No. 8,652,111 which is a divisional of U.S. patent application Ser. No. 12/537,797, filed Aug. 7, 2009, now U.S. Pat. No. 8,366,691, which claims the benefit, under 35 USC § 119(e), of the filing of U.S. Provisional Patent Application No. 61/087,377, filed Aug. 8, 2008, the disclosure of which is hereby incorporated herein by reference.

BACKGROUND

The present invention relates generally to medical treatment systems and devices, and more particularly, to reduced-pressure treatment systems with reservoir control.

The treatment of wounds is at times problematic. Proper care is required to minimize the possibility of infection and, preferably, to help stabilize the wound. Proper care typically involves keeping the wound clean and dry. Exudate from the wound is often removed and held away from the wound.

In recent times, reduced pressure has been used to help treat wounds and remove fluids including exudate. In many instances, reduced pressure has been applied with a negative pressure device that includes a foam pad placed on or in the wound and fluidly coupled to a reduced-pressure source. The reduced-pressure source typically has involved a vacuum pump that when activated delivers reduced pressure to the foam pad such that fluid is removed from the wound through the foam pad and transported through a tube to a fluid reservoir, such as a canister. The reservoir collects and holds the fluids removed from operation of the treatment system. When the reservoir is full of removed fluid, the reservoir is emptied and reengaged to the system or replaced. Efforts have been made to alert the patient when the reservoir is full.

BRIEF SUMMARY

Shortcomings with certain aspects of reduced-pressure treatment systems and systems for alerting a patient that a reservoir is full are addressed by the present invention as shown and described in a variety of illustrative embodiments herein. According to an illustrative embodiment, a reduced-pressure treatment system for treating a tissue site on a patient includes a manifold member for placing proximate the tissue site, an over-drape for providing a fluid seal over the manifold member and the patient, and a reduced-pressure subsystem for delivering reduced pressure to the over-drape. The reduced-pressure subsystem includes a reservoir having an interior space operable to contain fluids, a reduced-pressure delivery conduit in fluid communication with the interior space for delivering reduced pressure to the over-drape, a source conduit in fluid communication with the interior space, a pressure sensor conduit in fluid communication with the interior space, and a pressure sensor in fluid communication with the pressure sensor conduit. The reduced-pressure subsystem further includes a reduced-pressure source in fluid communication with the source conduit and operable to deliver reduced pressure to the source conduit, and a reduced-pressure control unit associated with the pressure sensor and reduced-pressure source. The reduced-pressure control unit is operable to receive pressure data from the pressure sensor and supply data from the reduced-pressure source and to determine when a reservoir-full/blockage condition exists.

According to another illustrative embodiment, a reduced-pressure system for providing reduced pressure and for receiving fluids includes a reservoir having an interior space operable to contain the fluids, a reduced-pressure delivery conduit in fluid communication with the interior space for delivering reduced pressure, a source conduit in fluid communication with the interior space, and a pressure sensor conduit in fluid communication with the interior space. The reduced-pressure system further includes a pressure sensor in fluid communication with the pressure sensor conduit and a reduced-pressure source in fluid communication with the source conduit and operable to deliver reduced pressure to the source conduit. The reduced-pressure system also includes a reduced-pressure control unit associated with the pressure sensor and reduced-pressure source that is operable to receive pressure data from the pressure sensor and supply data from the reduced-pressure source and to determine when a reservoir-full/blockage condition exists.

According to another illustrative embodiment, a reduced-pressure system includes a reservoir housing that forms an interior space and a reduced-pressure source for delivering reduced pressure. The reduced-pressure source is fluidly coupled to the interior space of the reservoir and is operable to deliver a reduced pressure to the interior space. The reduced-pressure source is responsive to a control signal. The reduced-pressure system further includes a supply sensor for measuring a supply rate of reduced pressure and operable to develop a signal I indicative of the supply rate, a pressure sensor conduit fluidly coupled to the interior space, and a pressure sensor in fluid communication with the pressure sensor conduit. The pressure sensor is operable to develop a signal P indicative of a pressure level in the pressure sensor conduit proximate the pressure sensor. The reduced-pressure system further includes a reduced-pressure control unit coupled to the supply sensor, pressure sensor, and the reduced-pressure source. The reduced-pressure control unit is operable to receive signal I from the supply sensor and signal P from the pressure sensor and to adjust the control signal to cause the reduced-pressure source to provide a desired pressure to the reservoir and to shutdown when the reservoir is full.

According to another illustrative embodiment, a method of detecting a fill status of a reservoir for use in treating a patient with a reduced-pressure treatment system includes the steps of: generating reduced pressure in fluid communication with the reduced-pressure treatment system, applying the reduced pressure to a tissue site, collecting fluid from the tissue site in the reservoir, and monitoring a pressure within the reservoir. The method further includes terminating the application of reduced pressure when the pressure in the reservoir decreases below a selected absolute value for specified time interval. The reservoir has a pressure sensor conduit in fluid communication with the reservoir and a supply conduit in fluid communication with the reservoir. The step of monitoring the pressure within the reservoir includes monitoring the pressure within the pressure sensor conduit.

According to another illustrative embodiment, a method of manufacturing a reduced-pressure system includes the steps of forming a reservoir having an interior space operable to contain fluids and fluidly coupling a reduced-pressure delivery conduit to the interior space. The reduced-pressure delivery conduit is for delivering a reduced pressure to a delivery site. The method of manufacturing further includes fluidly coupling a source conduit to the interior space, fluidly coupling a pressure sensor conduit to the interior space, and fluidly coupling a pressure sensor to the pressure sensor conduit. The method may also include providing a reduced-pressure source responsive to a control signal, coupling the reduced-pressure source to the source conduit, and providing a reduced-pressure control unit. The reduced-pressure control unit is operable to receive pressure data from the pressure sensor and supply data from the reduced-pressure source and to determine when a reservoir-full/blockage condition exists.

Other features and advantages of the illustrative embodiments will become apparent with reference to the drawings and detailed description that follow.

BRIEF DESCRIPTION OF THE DRAWINGS

A more complete understanding of the system, method, and apparatus of the present invention may be obtained by reference to the following Detailed Description when taken in conjunction with the accompanying Drawings wherein.

DETAILED DESCRIPTION OF THE PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
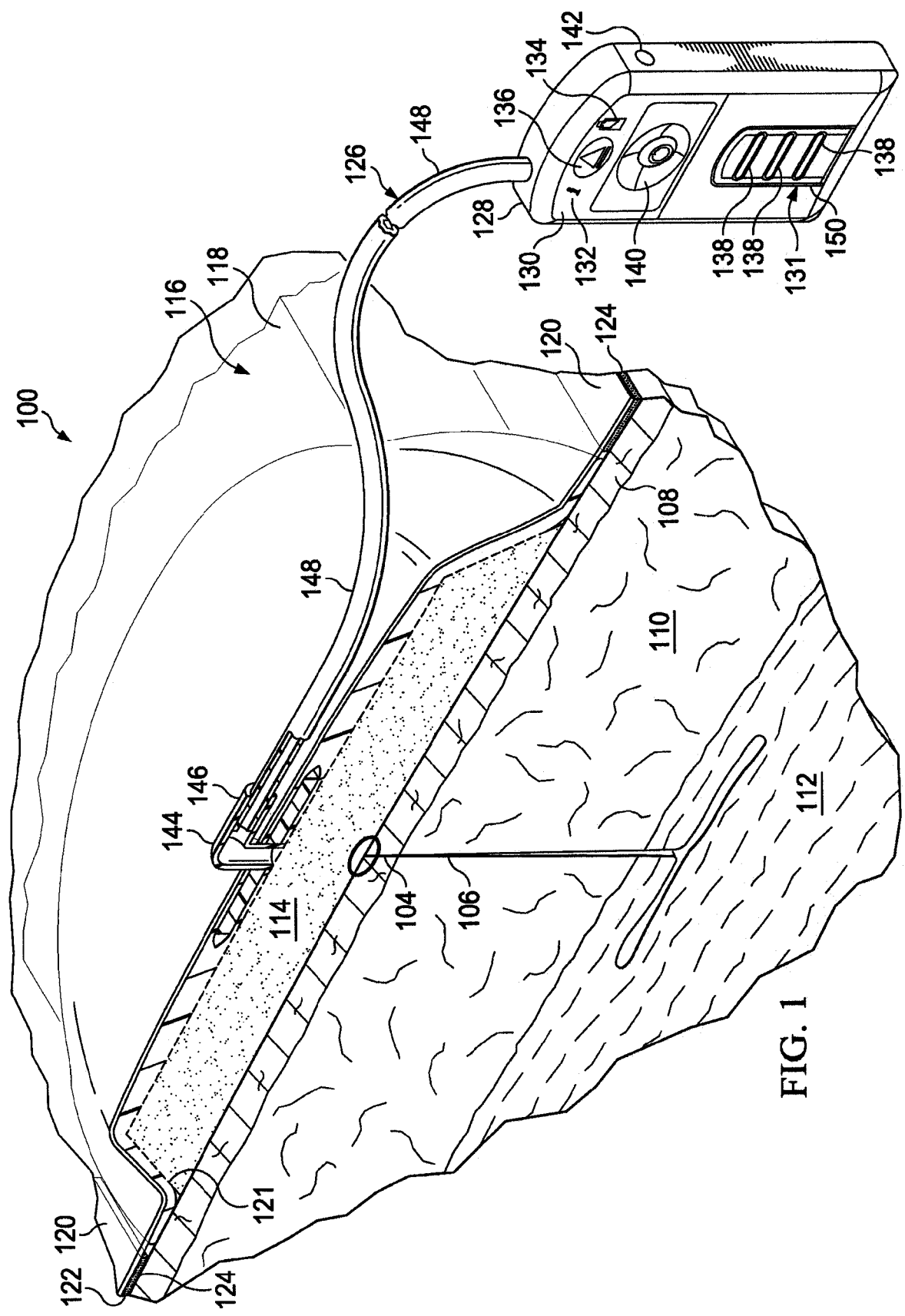
FIG. 1 is a schematic, perspective view of an illustrative embodiment of a reduced-pressure treatment system with reservoir control with a portion shown in cross section.

Referring to FIG. 1, an illustrative embodiment of a reduced-pressure treatment system 100 for treating a tissue site 106, e.g., a wound 104. The tissue site 106 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used herein, "or" does not require mutual exclusivity. The wound 104 may take numerous possible shapes and degrees, but in this illustrative example is shown as a linear wound, such as from a surgical procedure, through epidermis 108, dermis 110, and into a portion of the subcutaneous tissue 112. In this example, the reduced-pressure treatment system 100 is shown applied on top of the epidermis 108 and over the wound 104, but it is to be appreciated that the reduced-pressure treatment system 100 could be used with an open wound and could be placed, in part, below the epidermis in a wound bed. The reduced-pressure treatment system 100 may include a manifold member 114, a sealing subsystem 116, and a reduced-pressure subsystem 126. The reduced-pressure treatment system 100 may be built for relatively less money than conventional systems, achieve greater mechanical reliability, and operate in multiple orientations without false alarms.

In one illustrative embodiment, the manifold member 114 is made from a porous and permeable foam-like material and, more particularly, a reticulated, open-cell polyurethane or polyether foam that allows good permeability of wound fluids while under a reduced pressure. One such foam material that has been used is the VAC® Granufoam® Dressing available from Kinetic Concepts Inc. (KCI) of San Antonio, Tex. Any material or combination of materials may be used for the manifold material provided that the manifold material is operable to distribute the reduced pressure. The term "manifold" as used herein generally refers to a substance or structure that is provided to assist in applying reduced pressure to, delivering fluids to, or removing fluids from a tissue site. A manifold typically includes a plurality of flow channels or pathways that distribute fluids provided to and removed from the area of tissue around the manifold. The plurality of flow pathways may be interconnected. Examples of manifolds may include, without limitation, devices that have structural elements arranged to form flow channels, cellular foam, such as open-cell foam, porous tissue collections, and liquids, gels and foams that include or cure to include flow channels. The manifold material may also be a combination or layering of materials. For example, a first manifold layer of hydrophilic foam may be disposed adjacent to a second manifold layer of hydrophobic foam to form the manifold member 114.

The reticulated pores of the Granufoam® material, that are in the range of about 400 to 600 microns, are helpful in carrying out the manifold function, but again other materials may be used. A material with a higher, or lower, density (smaller pore size) than Granufoam® material may be desirable in some situations. The manifold member 114 may also be a reticulated foam that is later felted to thickness of about ⅓ its original thickness. Among the many possible materials, the following may be used: Granufoam® material or a Foamex technical foam (www.foamex.com). In some instances it may be desirable to add ionic silver to the foam in a microbonding process or to add other substances to the manifold member such as antimicrobial agents. The manifold member 114 could be a bio-absorbable or bio-inert material or an anisotropic material.

The sealing subsystem 116 includes an over-drape 118, or drape. The over-drape 118 covers the manifold member 114 and extends past a peripheral edge 121 of the manifold member 114 to form a drape extension 120. The drape extension 120 may be sealed against the patient's epidermis 108 by a sealing apparatus 122, such as a pressure-sensitive adhesive 124. The sealing apparatus 122 may take numerous forms, such as an adhesive sealing tape, or drape tape or strip; double-sided drape tape; adhesive 124; paste; hydrocolloid; hydrogel; or other sealing device. If a tape is used, the tape may be formed of the same material as the over-drape 118 with a pre-applied, pressure-sensitive adhesive. The pressure-sensitive adhesive 124 may be applied on a second, patient-facing side of drape extension 120. The pressure-sensitive adhesive 124 provides a substantially fluid seal between the over-drape 118 and the epidermis 108 of the patient. "Fluid seal," or "seal," means a seal adequate to hold reduced pressure at a desired site given the particular reduced-pressure subsystem involved. Before the over-drape 118 is secured to the patient, the pressure-sensitive adhesive 124 may have removable strips covering the adhesive 124.

The over-drape 118 may be an elastomeric material that provides a fluid seal. The sealing member may, for example, be an impermeable or semi-permeable, elastomeric material. "Elastomeric" means having the properties of an elastomer and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of sealing member materials include a silicone drape, 3M Tegaderm® drape, acrylic drape such as one available from Avery Dennison, or an incise drape.

The reduced-pressure subsystem 126 includes a reduced-pressure source 128, which may take many different forms. The reduced-pressure source 128 provides reduced pressure as a part of the reduced-pressure treatment system 100. The reduced-pressure source 128 may be any device for supplying a reduced pressure, such as a vacuum pump, wall suction, or other source. While the amount and nature of reduced pressure applied to a tissue site will typically vary according to the application, the reduced pressure will typically be between −5 mm Hg and −500 mm Hg and more typically between −100 mm Hg and −300 mm Hg.

As used herein, "reduced pressure" generally refers to a pressure less than the ambient pressure at a tissue site 106 that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the manifold member 114, reduced-pressure conduit 148, and proximate the tissue site 106. As the hydrostatic pressure around the tissue site 106 approaches the desired reduced pressure, the flow may subside, and the reduced pressure may be maintained. Unless otherwise indicated, values of pressure stated herein are gauge pressures. The reduced pressure delivered may be constant or varied (patterned or random) and may be delivered continuously or intermittently. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

In the illustrative embodiment of FIG. 1, the reduced-pressure source 128 is shown having a reservoir region 131, or canister region, with windows 138 providing a visual indication of the level of fluid within reservoir 150. An interposed membrane filter, such as hydrophobic or oleo-phobic filter, may be interspersed between a reduced-pressure delivery conduit, or tubing, 148 and the reduced-pressure source 128.

The reduced-pressure source 128 has a display 130, which may include an alarm light or information indicator 132, a battery light or indicator 134, a reservoir full/blocked light or indicator 136. The reduced-pressure source 128 may also include a power switch 140 and a speaker 142 for providing an audible alarm. In some embodiments, a keypad for entry of desired pressure or other information may also be provided. As described further below, the reduced-pressure subsystem 126 includes a reduced-pressure control unit analogous to a reduced-pressure control unit 260 in FIG. 2A.

The reduced pressure developed by the reduce-pressure source 128 is delivered through the reduced-pressure delivery conduit 148 to a reduced-pressure interface 144, which may be an elbow port 146. In one illustrative embodiment, the port 146 is a TRAC® technology port available from Kinetic Concepts Inc. of San Antonio, Tex. The reduced-pressure interface 144 allows the reduced pressure to be delivered to the sealing subsystem 116 and realized within an interior portion of sealing subsystem 116. In this illustrative embodiment, the elbow port 146 extends through the over-drape 118 and into the manifold member 114.

In operation, the reduced-pressure treatment system 100 is applied to treat the tissue site 106, e.g., the wound 104, by placing the manifold member 114 approximate wound 104, providing a fluid seal over the manifold member 114 and a portion of the epidermis 108 by using the sealing subsystem 116, attaching the reduced-pressure subsystem 126 and activating the reduced-pressure subsystem 126. The reduced-pressure subsystem 126 delivers reduced pressure to the manifold member 114, which distributes the reduced pressure to the wound site 106 as well as potentially providing other beneficial effects, such as a closing force in some applications when a closing dressing bolster is used. The reduced-pressure subsystem 126 may be used with a wound application as shown, and the reduced-pressure subsystem 126 may also be used with percutaneous applications, such as applying reduced pressure to a bone, tissue, or other wound site. In utilizing the reduced-pressure treatment system 100, the reduced-pressure treatment system 100 will continue to apply reduced pressure until the reservoir, or canister, 150 of the reduced-pressure source 128 becomes full. Because, it is desirable to minimize any breaks in the treatment, the status of the reservoir 150 may be visually monitored through the windows 138, but it is desirable to have the reduced-pressure subsystem 126 automatically alert the patient when the reservoir 150 is full or when a blockage has occurred such that reduced pressure is no longer being delivered. It may also be desirable to shutdown the reduced-pressure source 128 when the reservoir 150 is full or blocked.

Figure 2A:
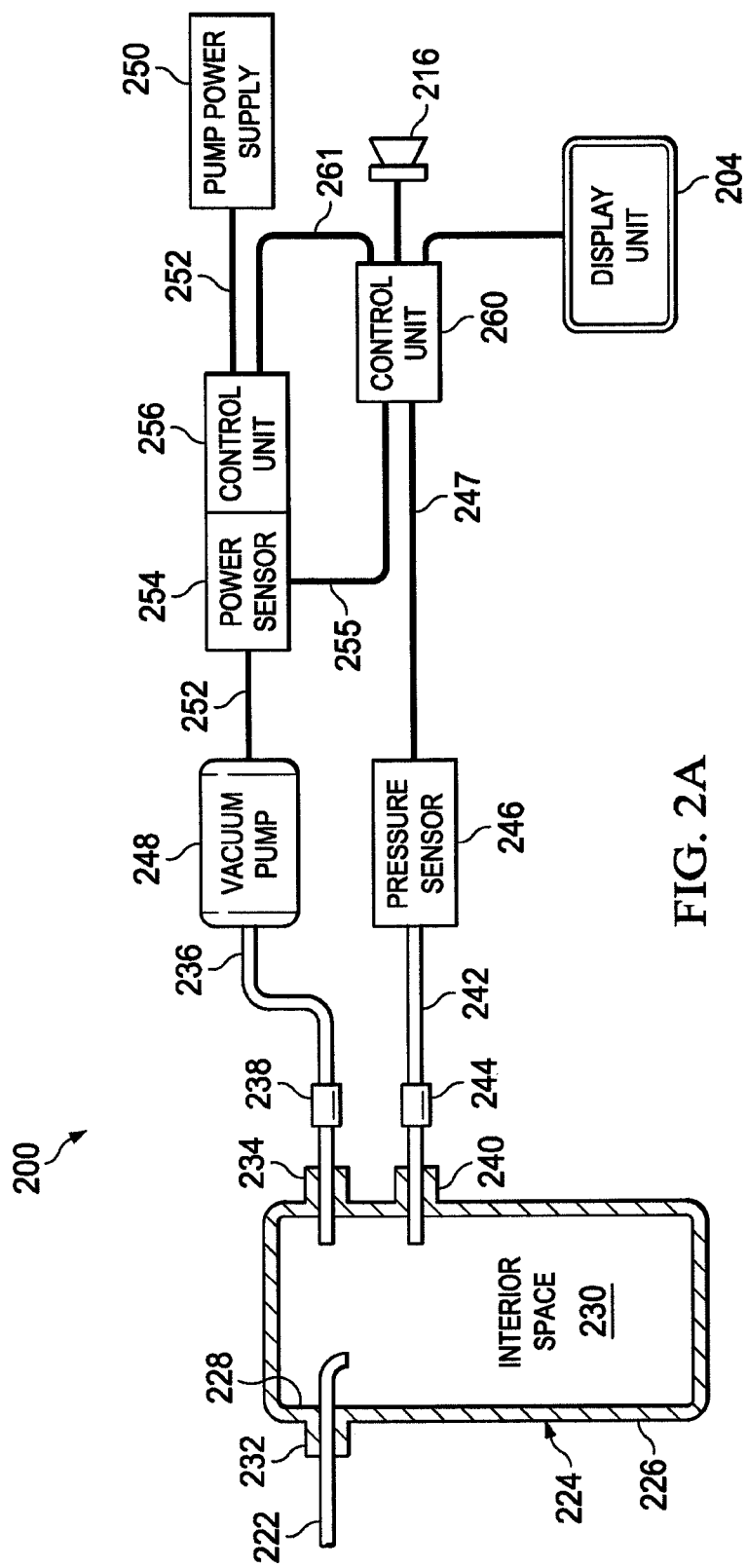
FIG. 2A is a schematic, diagram with a portion in cross-section of one illustrative embodiment of a reduced-pressure treatment system with reservoir control.

Referring now primarily to FIG. 2A, an illustrative embodiment of a reduced-pressure system 200 which may be used as the reduced-pressure subsystem 126 of the reduced-pressure treatment system 100 in FIG. 1 is presented. The reduced pressure is provided by the reduced-pressure system 200 and ultimately delivered by a reduced-pressure delivery conduit 222 for medical purposes to a delivery site, e.g., reduced-pressure interface 144 and tissue site 106 of FIG. 1. The reduced-pressure system 200 includes a reservoir 224 formed with a reservoir housing 226 that defines an interior space 230. The reservoir 224 may be any unit for holding fluids, such as a canister, bag, impervious envelope, etc. Proximate a top portion 228 (for the orientation shown with the unit standing parallel to the gravitational field), a number of ports may be formed through the reservoir housing 226. For example, a delivery-conduit port 232, a source port 234, and a sensor port 240 may be formed through the reservoir housing 226. The reduced-pressure delivery conduit 222 interfaces with the reduced-pressure delivery conduit port 232 such that the reduced-pressure delivery conduit 222 may be placed in fluid communication, or fluidly coupled, with the interior space 230. A source conduit 236 interfaces with the source port 234 to allow the source conduit 236 to be in fluid communication, or fluidly coupled, with the interior space 230. Similarly, a pressure sensor conduit 242 interfaces with the sensor port 240 to allow the pressure sensor conduit 242 to be placed in fluid communication, or fluidly coupled, with the interior space 230. While the sensor port 240 is shown slightly below the source port 234, it should be noted that these ports 234, 240 may be on the same vertical level in other embodiments.

The reduced-pressure delivery conduit 222 delivers reduced pressure for medical purposes and receives fluid, such as exudate, that enter into the interior space 230. A number of filters, e.g., hydrophobic filters or odor filters, may be desired on the conduits 222, 236, and 242. For example, the source conduit 236 is shown with a first filter unit 238, and the pressure sensor conduit 242 is shown with a second filter unit 244. While filter units 238 and 244 are shown as single units, it is to be understood that a plurality of filters may make up each filter unit.

The pressure sensor conduit 242 provides fluid communication from the interior space 230 to a pressure sensor 246. The pressure sensor 246 may be any device (or devices) that is capable of sensing the pressure in the pressure sensor conduit 242 and developing a responsive single which may be analog or digital, and delivering the signal by a communication conduit 247 to the reduced-pressure control unit 260. In an alternative embodiment, the pressure sensor 246 may be or include a pneumatic regulator that is coupled to a reduced-pressure source, e.g., a vacuum pump 248, regulated wall suction, mechanical device, or other reduced pressure apparatus.

The source conduit 236 is in fluid communication with the interior space 230 and is also in fluid communication with a reduced-pressure source, e.g., the vacuum pump 248. The vacuum pump 248 works to generate the reduced pressure that is introduced into the source conduit 236. In the illustrative embodiment, the vacuum pump 248 is electrically powered as indicated by a first power line 252. The first power line 252 is electrically coupled to a pump power supply 250. The pump power supply 250 may be a battery supply or a conditioned power from another source. A portion of the first power line 252 may include a power sensor 254 and a current control unit 256. The power sensor 254 may be any device that is used to determine the amount of power being supplied to the vacuum pump 248. For example, the power sensor 254 may be a current sensor operable to produce a current signal or supply data signal I. More generally, the supply data signal may be produced that provides information on the rate of delivery or attempted delivery of reduced pressure. In one illustrative embodiment, the supply data signal may be the current supplied to a vacuum pump. In another illustrative embodiment, the supply data signal may be a signal indicative of a valve opening on a regulated wall suction unit. Whether a current signal, other power data, or supply data developed by power sensor 254 or other sensor that measures a signal correlated to a supply rate, the resulting signal I is delivered by a communication conduit 255 to the reduced-pressure control unit 260.

The reduced-pressure control unit 260 contains circuitry or a microprocessor that controls functions within the reduced-pressure system 200. The reduced-pressure control unit 260 receives a pressure signal P from the communication conduit 247 and supply data, e.g. signal I, from the communication conduit 255, which is coupled to a sensor, e.g., the power sensor 254. The reduced-pressure control unit 260 determines if the interior space 230 of the reservoir 224 is substantially full or if a conduit 222, 236, 242 is blocked. If the reduced-pressure control unit 260 determines that the interior space 230 is full or conduits blocked, the reduced-pressure control unit 260 may send an alarm to a speaker 216 as well as providing an alarm signal to a display unit 204. The reduced-pressure control unit 260 may also develop a pump control signal PC that is delivered by a communication conduit 261 to the current control unit 256 and may be used to increase the power to the vacuum pump 248 or to reduce or stop the vacuum pump 248. Similarly, if a different reduced pressure source is used, a control signal may be used to adjust the reduced-pressure source. In alternative embodiments, it may be desirable to provide other inputs or data to the reduced-pressure control unit 260, such as a temperature input that may be used to predict the viscosity of the fluid being captured within the interior space 230 and to further adjust parameters for determining when the reservoir is full, such as the time interval used.

Figure 2B:
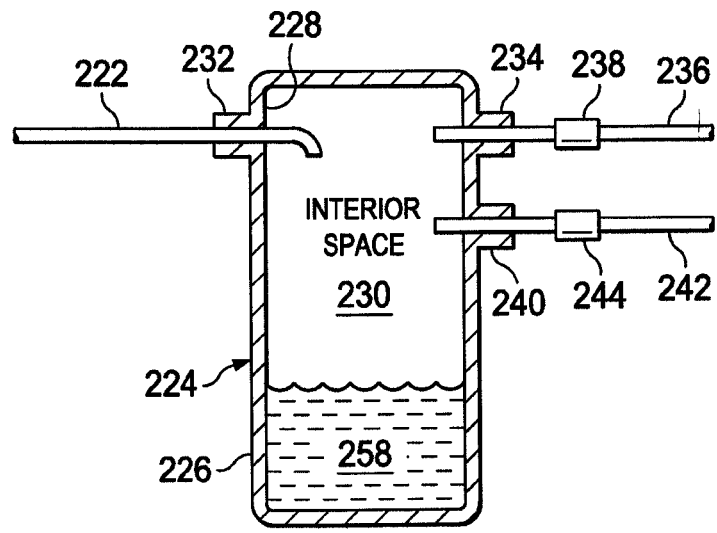
FIGS. 2B and 2C are schematic, elevational, cross-sectional views of a portion of the reduced-pressure system of FIG. 2A.
Figure 2C:
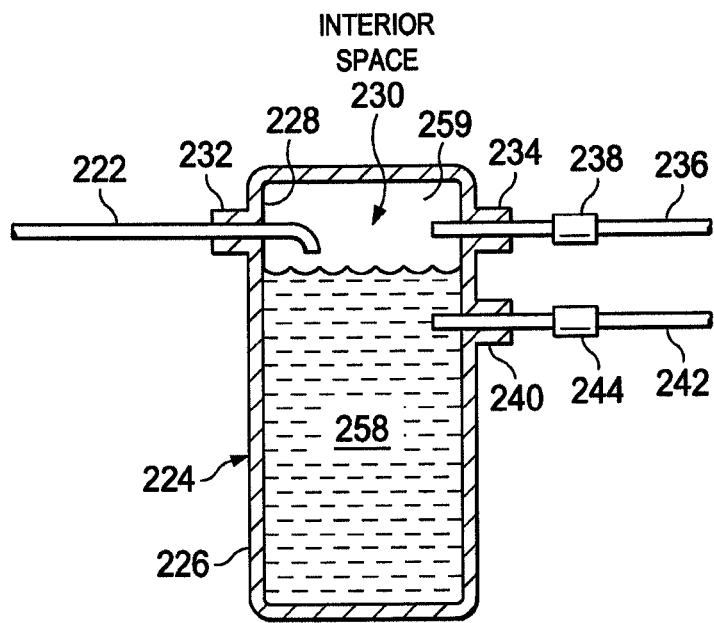

Referring now primarily to FIGS. 2A, 2B, 2C, in operation, the reduced-pressure system 200 is initially activated and has unblocked conduits 222, 236, 242 and an empty interior space 230. Reduced pressure is delivered to the interior space 230 and is transmitted to the reduced-pressure delivery conduit 222 and to a desired site. FIG. 2A shows this initial state with the reservoir 224 empty. As the reduced pressure is delivered for treatment of a tissue site, e.g., a wound, on a patient, various fluids are typically received through the reduced-pressure delivery conduit 222 and are delivered into the interior space 230 where the fluid collects. FIG. 2B shows the fluid 258 collecting in a bottom portion of the interior space 230. The reduced-pressure control unit 260 continues to operate the vacuum pump 248 and pressure sensor 246 continues to monitor the pressure experienced within the pressure sensor conduit 242 which typically corresponds to the pressure within the interior space 230. The reduced pressure is monitored to determine that the pressure is within a desired range or at least above a threshold. When, however, the fluid 258 fills or substantially fills the interior space 230 such that the sensor port 240 becomes covered by the fluid 258, the incompressible nature of the fluid 258 will cause the pressure sensor 246, which is in fluid communication with the interior space 230, to experience a reduction in reduced pressure (a rise in absolute pressure). A remaining void space 259 is shown.

In one illustrative embodiment, if the reduced-pressure control unit 260 determines that, despite increased power or passage of a wait time, the desired reduced pressure within interior space 230 is below the desired reduced pressure level, the reduced-pressure control unit 260 will send an alarm signal or send a pump control signal to the current control unit 256 to shut down vacuum pump 248. The reduced-pressure control unit 260 may shut down or send an alarm if the reduced-pressure control unit 260 is unable to increase the reduced pressure (lower the absolute pressure) within interior space 230 due to a blockage in one of the conduits 222, 236, 242. Additional examples how the reduced-pressure control unit 260 may operate are provided in connection with FIGS. 3 and 4.

Figure 3:
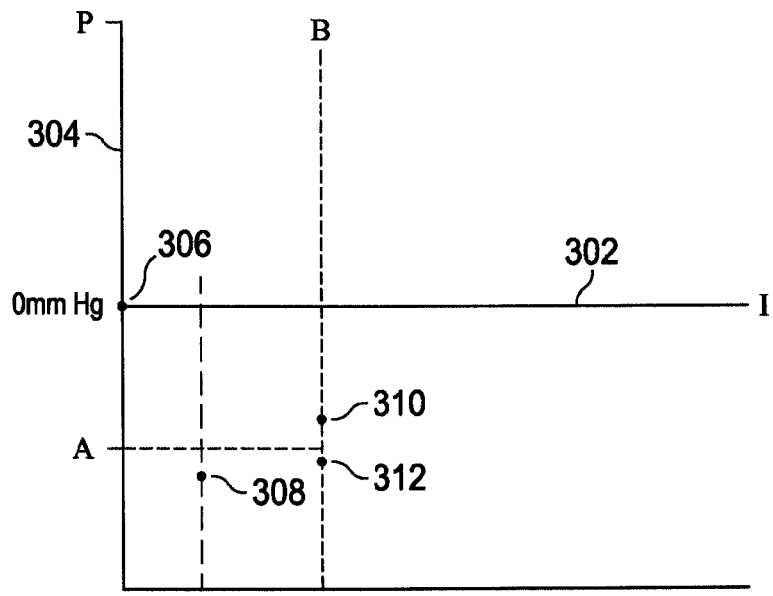
FIG. 3 is a representative graph presenting illustrative operational parameters of a reduced-pressure treatment system according to one illustrative embodiment.

Referring now primarily to FIG. 3, a schematic graph is presented showing operational parameters that may be used by the reduced-pressure control unit 260 in the reduced-pressure system 200 in FIGS. 2A-2C with respect to pressure and power. Power is represented by the current in this illustrative embodiment. The graph has an abscissa axis 302 and an ordinate axis 304. The abscissa axis 302 shows a relative measurement of the power provided to the vacuum pump 248 in the reduced-pressure system 200. The ordinate axis 304 represents the pressure measured by the pressure sensor 246 and that generally corresponds to the reduced pressure delivered into the interior space 230 of the reservoir 224.

Referring to FIG. 2A and FIG. 3, just before the reduced-pressure system 200 is activated, the reduced-pressure system 200 may be represented on the graph of FIG. 3 at the first point 306—no reduced pressure (gauge pressure) and no power. Once activated, the vacuum pump 248 runs until the reduced pressure exceeds the selected level A and is then turned off. The selected level A may be pre-set or may be entered by a user or healthcare provider. Thus, before the vacuum pump 248 is temporarily deactivated, the reduced pressure may be represented at a second point 308. The second point 308 shows that the reduced pressure has now exceeded the threshold selected level A and shows that the vacuum pump 248 is currently operating because of the positive current measurement on the abscissa. At this time, the reduced-pressure control unit 260 can tell the vacuum pump 248 to shut down, such as by sending a pump control signal PC to the current control unit 256. The vacuum pump 248 may remain off until the pressure sensor 246 determines that the reduced pressure has decreased below the threshold level A or some other set level. At that time, the vacuum pump 248 will be reactivated to again restore the pressure measured by the pressure sensor 244, which typically corresponds with the pressure within interior space 230, to again exceed level A.

In one illustrative embodiment, if the source conduit 236 begins to experience partial blocking, the previously used level of reduced pressure supplied by vacuum pump 248 may not be able to cause the reduced pressure in the interior space 230 (as measured in the pressure sensor conduit 242 by the pressure sensor 244) to exceed the threshold level A. Before concluding that the reservoir, or canister, 224 is full and shutting down, the power level of the vacuum pump 248 may first be increased by the reduced-pressure control unit 260 for a time. The power level of the vacuum pump may be increased all the way to a full power level or a selected level as shown by reference line B on the graph. Thus, in one example the reduced-pressure control unit 260 may determine that the pressure at the pressure sensor 246 is below the pressure level A and that the reduced pressure is not increasing. Then, full power or a maximum power setting B may be applied to the vacuum pump 248 such that the reduced-pressure system 200 may be represented on the graph by a third point 310. If partial blockage is the main issue that had otherwise kept the pressure from fully responding, the vacuum pump 248 at the increased full power level may be able to move to a fourth point 312, which is beyond pressure threshold level A and the vacuum pump 248 will shut down until the pressure decreases below level A again. If the blockage of the source conduit 236 is such that even full power does not move the pressure beyond level A after a given time, the alarm is signaled and the vacuum pump 248 is shut down. Note that as shown in FIG. 2C, when the incompressible fluid 258 covers the sensor port 240, the increased power to the vacuum pump 248 will result in lowering the pressure in the remaining void space 259 of reservoir 224, but will not increase the reduced pressure and thus will not cause the pressure measured by pressure sensor 246 to be beyond level A. Accordingly, the system 200, and particularly the vacuum pump 248, will shut down and give the full reservoir/blocked indication.

Figure 4:
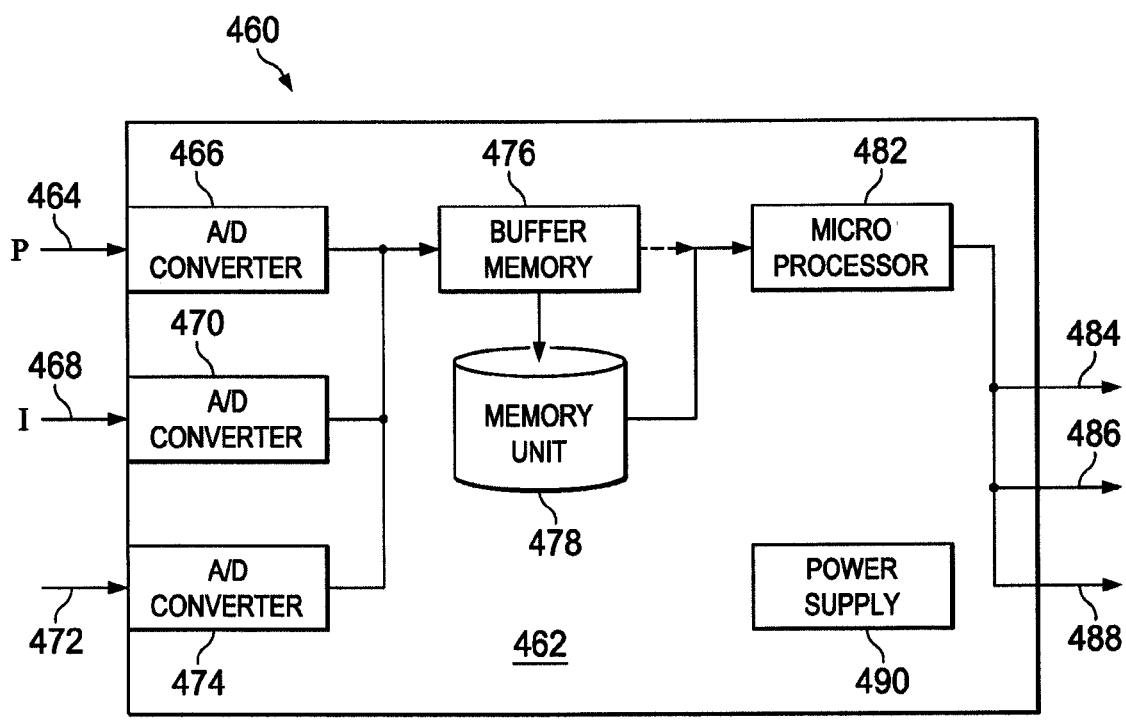
FIG. 4 is a schematic diagram of an illustrative embodiment of a reduced-pressure control unit.

Referring now primarily to FIG. 4, an illustrative embodiment of a reduced-pressure control unit 460 is presented. The reduced-pressure control unit 460 includes a housing unit 462, which contains various components for controlling a reduced-pressure system, such as system 200 of FIG. 2A-2C. The reduced-pressure control unit 460 may receive a number of different input signals from input devices. The reduced-pressure control unit 460 is shown with a first input 464, which in this illustration is a pressure signal P representative of the pressure within the interior space of the reservoir as measured by a pressure sensor in a pressure sensor conduit. If the pressure signal supplied to the first input 464 is not already digitized, a first analog-to-digital converter 466 may be included to receive and convert the pressure signal to a digital signal. A second input 468 may be included. In this illustration, the second input 468 is a supply signal, e.g., a signal representative of the power data to the pump and in particular may be a signal I. As before, if the supply signal I is not already in a digitized form, a second analog-to-digital converter 470 may be included to convert the signal to a digital format.

Similarly, a third input signal 472 is shown and is merely representative of other signals that may be provided to the reduced-pressure control unit 460. For example, the third input signal 472 may be a temperature signal that reflects the temperature within the fluid in the reservoir. The fluid temperature might affect the viscosity of the fluid and in turn might influence such parameters as the interval time for waiting on responses within the reduced-pressure system. If the representative third input signal 472 is not already in a digitized form, another analog-to-digital converter 474 may be included.

The signals received in the input signals 464, 468, 472, (and converted if needed) may be delivered to a buffer memory 476 and either supplied to a memory unit 478 or directly delivered to a microprocessor 482. It may be desirable to keep a recording of the input data to allow different determinations, such as whether or not the pressure is rising or decreasing. The memory unit 478 may also be used to determine if no pressure change has been experienced over an extended time period while the reduced-pressure source has been off. In that case, it may be desirable for the reduced-pressure control unit 460 to provide a warning light that the reduced-pressure delivery conduit, e.g. reduced-pressure delivery conduit 222 FIG. 2A, may be blocked.

The microprocessor 482 is operable to carry out a number of different determinations as to when the vacuum pump should be increased in power, shut down, or when an alarm signal or other signals should be produced as will be explained in connection with FIG. 5. The microprocessor 482 has a number of outputs. A first output 484 is a pump control signal that may be delivered to control the vacuum pump. For example, the pump control signal 484 may be delivered to the current control unit 256 in FIG. 2A to adjust the power to the vacuum pump 248 or to turn the vacuum pump 248 off. In embodiments with other reduced pressure sources, a control signal may be used to adjust the supply rate. The microprocessor 482 may also provide a second output 486, which may be an alarm signal. The alarm signal may activate an audible alarm, e.g. speaker 142 in FIG. 1. A third output 488 is a representative output signal that may control other features, such as providing a status light on a display, e.g. light or indicator 132 or 136 in FIG. 1. A power supply 490 supplies power to various components within the reduced-pressure control unit 460 and may be a battery or may be conditioned power from another source.

For control units that utilize a microprocessor, such as reduced-pressure control unit 460 of FIG. 4, the microprocessor, e.g., microprocessor 482, may be designed to be used in conjunction with a memory device, e.g. buffer memory 476 or memory unit 478, to conduct a number of different operations in using the input signals 464, 468, and developing of appropriate output signals, e.g. signals 484, 486, 488.

Figure 5:
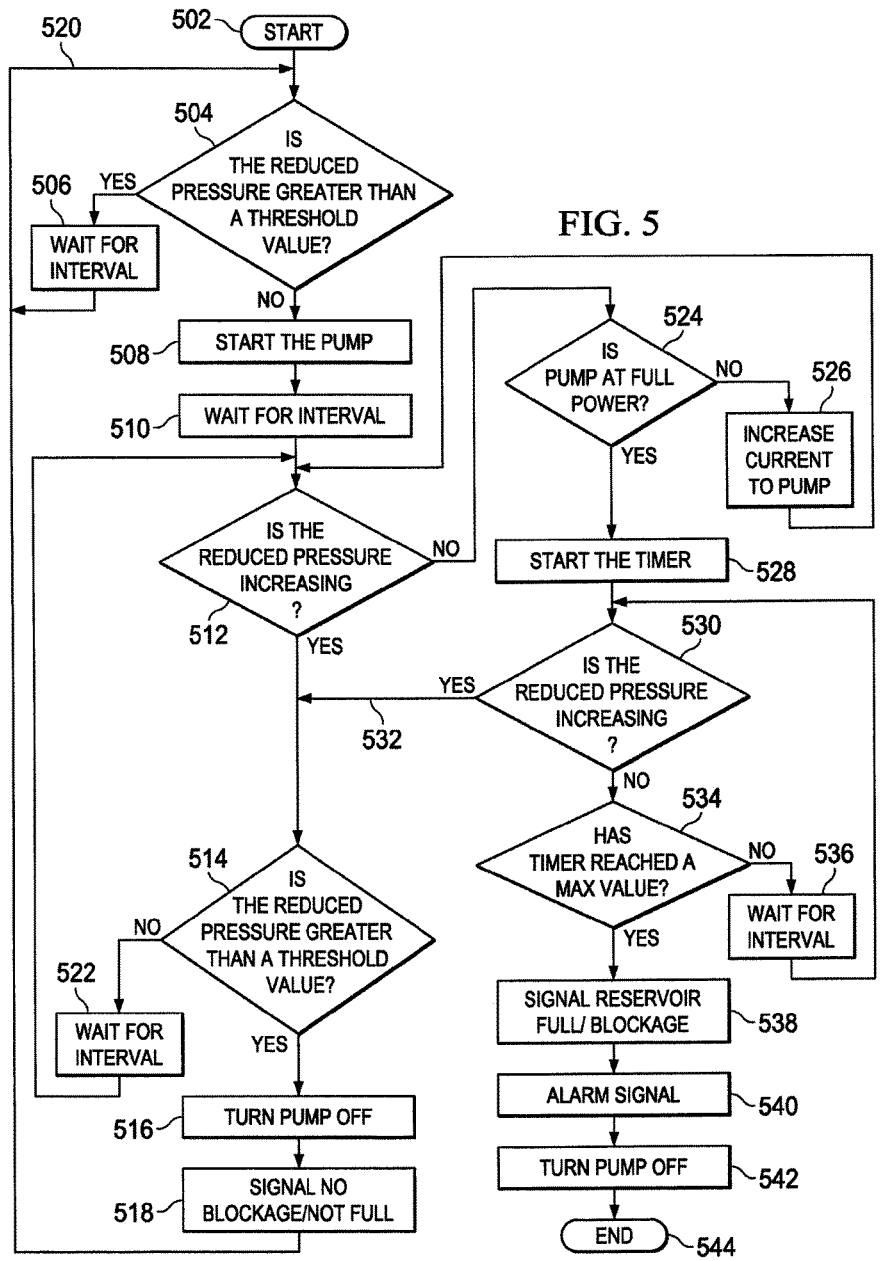
FIG. 5 is an illustrative flow chart of one possible approach to the logic incorporated into a reduced-pressure control unit in one illustrative embodiment.

Referring now primarily to FIG. 5, one illustrative presentation of the possible logic or operation that may be used with a control unit is presented. The operation begins at step 502 and proceeds to decision step 504 where a question is asked: is the reduced pressure from a pressure sensor in a pressure sensor conduit greater than threshold value? (The reduced pressure in the pressure sensor conduit typically is the same as in the reservoir to which the pressure sensor conduit is fluidly coupled). In other words, is the absolute value of the negative gauge pressure greater than the threshold value? With reference to FIG. 3, the question is asking whether or not the pressure point is below the threshold value line A. If the answer is in the affirmative, an increase in the reduced pressure is not necessary, and the system can wait. Accordingly, the flow proceeds to step 506 where the system waits for a certain time interval before again returning to decision step 504. This time interval and the others may be pre-programmed or may be entered by a healthcare provider or user.

If the response to decision step 504 is in the negative, additional reduced pressure is desired and the vacuum pump is activated at step 508. Then, the vacuum pump or reduced-pressure source is allowed to act for a certain time interval at step 510 before the system goes to decision step 512 where the following question is asked: is the reduced pressure increasing? In other words, is the absolute value of the reduced pressure in the reservoir increasing—taking on a larger number? If so, the system proceeds to decision step 514, which again asks if the reduced pressure is greater than a threshold value. If the answer is in the affirmative, the system proceeds to step 516 and the pump or reduced-pressure source is turned off. In that case, the system would update the signal indicating no blockage/not full in step 518 and would return along path 520 to go back to decision step 504.

If the response to decision step 514 is in the negative, the system may wait for a specified time interval at step 522 before again returning to decision step 512. This forms a loop and the loop can continue until the threshold value is reached or until the reduced pressure is no longer increasing. Once the pressure is no longer increasing, the answer at decision step 512 is in the negative, and the system proceeds to decision step 524. Decision step 524 asks whether or not the pump is at full power (or reduced-pressure source at maximum reduced pressure). If the answer is in the negative, the power to the pump is increased at step 526, and if in the affirmative, a timer is started at step 528. Then, decision step 530 is reached, and decision step 530 asks the question: is the reduced pressure increasing? If the answer is in the affirmative, the analysis continues along path 532 to decision step 514. If the answer is in the negative, the process continues to decision step 534. Decision step 534 asks if the timer started at 528 has reached the maximum timer value. If the timer has not, additional time is taken with step 536. If the timer has, the process has timed out and the process proceeds to step 538 where a signal indicating reservoir (canister) full/blockage is sent. In addition, an alarm signal may be sent in step 540. The vacuum pump or reduced-pressure source may then be turned off at step 542. The process ends at step 544. It will be appreciated that the reservoir (canister) full/blockage signal is given when either the reservoir is deemed full or when a blockage exists. Either way, the system is unable to restore the pressure in the reservoir and a reservoir-full/blockage condition exists. This logic is only one of the many ways that the control unit may be programmed.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

What is claimed is:

1. A control unit for controlling a reduced-pressure source, the control unit configured to:
    monitor a pressure signal correlated to a reduced pressure within a reservoir;
    receive a supply signal correlated to a supply rate of reduced pressure;
    determine if an absolute value of the pressure signal is below a predetermined threshold value; and
    terminate a supply of reduced pressure if the absolute value of the pressure signal does not reach the predetermined threshold value with an increased supply rate of reduced pressure during a specified time interval.

2. The control unit of claim 1, wherein the control unit is further configured to activate an alarm signal if the pressure signal does not rise in absolute value with the increased supply rate of reduced pressure.

3. The control unit of claim 2, wherein the alarm signal indicates a blockage condition.

4. The control unit of claim 3, wherein the blockage condition is a full reservoir.

5. The control unit of claim 1, wherein the supply signal is correlated to power supplied to the reduced-pressure source.

6. The control unit of claim 1, wherein the supply signal is correlated to a current supplied to the reduced-pressure source.

7. The control unit of claim 1, wherein the supply signal is indicative of a valve opening on the reduced-pressure source.

8. A reduced-pressure control unit configured to:
    receive a pressure signal from a pressure sensor, wherein the pressure signal is correlated to a reduced pressure in a reservoir;
    receive a supply signal from a supply sensor, wherein the supply signal is correlated to a supply rate of reduced pressure to the reservoir; and
    generate a control signal for a reduced-pressure source to terminate a supply of reduced pressure if an absolute value of the pressure signal does not reach a predetermined threshold value with an increased supply rate of reduced pressure during a specified time interval.

9. The reduced-pressure control unit of claim 8, wherein generating a control signal comprises determining if a blockage condition exists based on the pressure signal and the supply signal.

10. The reduced-pressure control unit of claim 8, wherein the supply signal is correlated to power supplied to the reduced-pressure source.

11. The reduced-pressure control unit of claim 8, wherein the supply signal is correlated to current supplied to the reduced-pressure source.

12. The reduced-pressure control unit of claim 8, wherein the supply signal is indicative of a valve opening on the reduced-pressure source.

13. The reduced-pressure control unit of claim 9, wherein the reduced-pressure control unit is further configured to generate an alarm signal if a blockage condition exists.

14. A control unit configured to control a reduced-pressure source, the control unit comprising:

a microprocessor operable to generate a control signal for the reduced-pressure source;

a memory device associated with the microprocessor;

a plurality of input devices associated with the microprocessor, the input devices configured to receive a pressure signal and a supply signal; and an output device associated with the microprocessor, the output device configured to receive the control signal from the microprocessor and make the control signal available to the reduced-pressure source;

wherein the microprocessor is configured to terminate a supply of reduced pressure if an absolute value of the pressure signal does not reach a predetermined threshold value with an increased supply rate of reduced pressure during a specified time interval.

* * * * *